US010555915B2

(12) United States Patent
Kopke et al.

(10) Patent No.: US 10,555,915 B2
(45) Date of Patent: *Feb. 11, 2020

(54) METHODS FOR TREATING ACUTE ACOUSTIC TRAUMA

(75) Inventors: Richard Dana Kopke, Oklahoma City, OK (US); Robert A. Floyd, Oklahoma City, OK (US)

(73) Assignees: Hough Ear Institute, Oklahoma City, OK (US); Oklahoma Medical Research Foundation, Oklahoma City, OK (US)

(*) Notice: Subject to any disclaimer, the term of this patent is extended or adjusted under 35 U.S.C. 154(b) by 461 days.

This patent is subject to a terminal disclaimer.

(21) Appl. No.: 13/391,772

(22) PCT Filed: Aug. 24, 2010

(86) PCT No.: PCT/US2010/046420
§ 371 (c)(1),
(2), (4) Date: Feb. 22, 2012

(87) PCT Pub. No.: WO2011/028503
PCT Pub. Date: Mar. 10, 2011

(65) Prior Publication Data
US 2012/0172435 A1    Jul. 5, 2012

Related U.S. Application Data

(60) Provisional application No. 61/274,118, filed on Aug. 24, 2009.

(51) Int. Cl.
| A61K 31/10 | (2006.01) |
| A61K 31/198 | (2006.01) |
| A61K 9/00 | (2006.01) |

(52) U.S. Cl.
CPC ............ *A61K 31/10* (2013.01); *A61K 9/0053* (2013.01); *A61K 31/198* (2013.01)

(58) Field of Classification Search
CPC ... A61K 31/205; A61K 31/198; A61K 31/185
See application file for complete search history.

(56) References Cited

U.S. PATENT DOCUMENTS

| 5,475,032 | A  | * | 12/1995 | Carney | ......................... 514/576 |
| 6,177,434 | B1 | * | 1/2001  | Kopke et al. | ................... 514/46 |
| 6,649,621 | B2 | * | 11/2003 | Kopke et al. | ............. 514/266.1 |
| 2002/0177558 | A1 | | 11/2002 | Meyerhoff et al. | |
| 2003/0191064 | A1 | | 10/2003 | Kopke | |
| 2004/0247570 | A1 | | 12/2004 | Miller et al. | |
| 2005/0054646 | A1 | | 3/2005 | Stephenson et al. | |
| 2008/0107641 | A1 | | 5/2008 | Kuebler | |
| 2008/0161406 | A1 | | 7/2008 | Andersson et al. | |
| 2009/0306225 | A1 | | 12/2009 | Lichter et al. | |
| 2014/0302322 | A1 | | 10/2014 | Silvy et al. | |

FOREIGN PATENT DOCUMENTS

| WO | WO 2005/079270 A2 | 9/2005 |
| WO | WO2007119578 | 10/2007 |
| WO | WO2008013866 | 1/2008 |

OTHER PUBLICATIONS

STN Registry No. 168021-79-2. Retrieved from STN [Online]. Retrieved Oct. 25, 2012 One Page.*
Williams et al. "Investigating the Free Radical Trapping Ability of NXY-059, S-PBN and PBN". Free Radical Research. Sep. 2007; 41(9):1047-1052.*
Kuokkanen et al. "Efficiency of Hyperbaric Oxygen Therapy in Experimental Acute Acoustic Trauma from Firearms". Acta Otolaryngol. 2000; Suppl 543:132-134.*
Dehouck et al. "In Vitro Blood-Brain Barrier Permeability and Cerebral Endothelial Cell Uptake of the Neuroprotective Nitrone Compound NXY-059 in Normoxic, Hypoxic and Ischemic Conditions". Brain Research, 2002; 955:229-235.*
Swan et al. "Inner Ear Drug Delivery for Auditory Applications." Advanced Drug Delivery Reviews. 2008; 60:1583-1599.*
Maples et al. "Comparison of the Radical Trapping Ability of PBN, S-PBN and NXY-059". Free Radical Research. 2001; 34:417-426.*
Floyd et al. "Anti-Cancer Activity of Nitrones in the ApcMin/+ Model of Colorectal Cancer". Free Radical Research. Jan. 2010; 44(1):108-117.*
Ginsberg MD. "Life After Cerovive: A Personal Perspective on Ischemic Neuroprotection in the Post-NXY-059 Era". Stroke. 2007; 38:1967-1972.*
Kuroda et al. "Neuroprotective Effects of a Novel Nitrone, NXY-059, After Transient Focal Cerebral Ischemia in the Rat". Journal of Cerebral Blood Flow and Metabolism. 1999; 19:778-787.*
Pardridge WM. "CNS Drug Design Based on Principles of Blood-Brain Barrier Transport". Journal of Neurochemistry. 1998; 70:1781-1792.*
Suzuki, Mitsuya et al.; Effect of Noise Exposure on Blood-Labyrinth Barrier in Guinea Pigs; Hearing Research 164 (2002) 12-18.
Mom, Thierry et al.; Cochlear Blood Supply: An Update on Anatomy and Function; Fr ORL-2005-81-88.
Nuttal, Alfred L.; Sound-Induced Cochlear Ischemia/Hypdxia as a Mechanism of Hearing Loss; Noise and Health—1999—vol. 2, Issue 5—17-31.
Culot, Maxime et al.; Cerebrovascular Protection as a Possible Mechanism for the Protective Effects of NXY-059 in Preclinical Models: An In Vitro Study; Brain Research 1294 (2009) 144-152.
Lundquist, Stefan et al.; Penetration of NXY-059 Through the Blood Brain Barrier In Vitro; Otologic Pharmaceutics; pp. 1-8, 1998.
Lapchek, Paul A. et al; Development of the Nitrone-Based Spin Trap Agent NXY-059 to Treat Acute Ischemic Stroke; CNS Drug Reviews, vol. 9, No. 3, 2003; 253-262.

(Continued)

*Primary Examiner* — Leslie A. Royds Draper
(74) *Attorney, Agent, or Firm* — Gilberto M. Villacorta; Tianran Yan; Foley & Lardner LLP

(57) ABSTRACT

The current invention provides methods and compositions for treating sensorineural hearing loss including but not limited to acute acoustic trauma (AAT). The composition 2,4-disulfonyl α-phenyl tertiary butyl nitrone and N-acetylcysteine (NAC). Preferably, the compositions for treating AAT will be administered orally. However, other methods which deliver the compositions for treating AAT systemically to the body should work equally well.

10 Claims, 6 Drawing Sheets

(56) References Cited

OTHER PUBLICATIONS

Diener, Hans-Christoph et al.; NXY-059 for the Treatment of Acute Stroke: Pooled Analysis of the Saint I and II Trials; Stroke; Journal of the American Heart Association; Jun. 2008; 1751-1758.

Folbergrova, Jaroslava et al; N-Tert-Butyl-Phenylnitrone Improves Recovery of Brain Energy State in Rats Following Transient Focal Ischemia; Proc. Natl. Acad. Sci. USA 92 (1995); 5057-5061.

Shi, Xiaorui et al.; Altered Expression of Inducible Initric Oxide Synthase (iNOS) in the Cochlea; Hearing Research 177 (2003) 43-52.

Laurell, Goran F.E. et al.; Intact Blood-Perilymph Barrier in the Rat After Impulse Noise Trauma; Acta Oto-Laryngologica, 2008; 128: 608-612.

Tabuchi, Keiji et al.; Ischemia-Reperfusion Injury of the Cochlea: Pharmacological Strategies for Cochlear Protection and Implications of Glutamate and Reactive Oxygen Species; Current Neuropharmacology, 2010, 8, 128-134.

Floyd, Robert et al.; Translational Research Involving Oxidative Stress and Diseases of Aging; Free Radic Biol Med. Sep. 1, 2011; 51(5): 931-941.

The Science: Otologic Pharmaceutics; 6 pages, 2014.

Ewert, Donald L. et al.; Antioxidant Treatment Reduces Blast-Induced Cochlear Damage and Hearing Loss; Hearing Research 285 (2012) 29-39.

MCE Medchem Express; NXY-059; http://www.medchemexpress.com/nxy-059.html, 2014.

Rso, Deepa et al.; Protective Effects of Phenyl-N-Tert Butylnitrone on the Potentiation of Noise-Induced Hearing LSOSS by Carbon Monoxide; Toxicology and Applied Pharmacology 167, 125-131 (2000); 125-131.

Final Office Action issued in related U.S. Appl. No. 15/495,897, dated Apr. 12, 2018.

* cited by examiner

US 10,555,915 B2

METHODS FOR TREATING ACUTE ACOUSTIC TRAUMA

RELATED

The present application claims priority to PCT Application No. PCT/US10/046420 entitled METHODS OF TREATING ACUTE ACOUSTIC TRAUMA filed Aug. 24, 2010, which claims priority to U.S. Provisional Patent Application Ser. No. 61/274,118 filed on Aug. 24, 2009.

BACKGROUND OF THE INVENTION

Acute acoustic trauma (AAT) is known to cause permanent hearing loss. Hearing loss from AAT is also enhanced by simultaneous exposure to other toxins such as low levels of carbon monoxide or acrylonitrile. Recent studies indicate that free radical processes are involved in the AAT-induced hearing loss. At this time an FDA approved treatment does not exist for the treatment of AAT or other causes of sensorineural hearing loss (SNHL). Thus, a substantial need exists for treatment methods and compounds suitable for treating victims of AAT events. Additionally, a need exists for treatment of all forms of SNHL.

In a co-pending application, U.S. Ser. No. 12/374,970, filed on Jan. 23, 2009, previously published as PCT Application, Publication No. 2008/013866, the inventors describe the ability to treat AAT-induced hearing loss with the preferred combination of 4-hydroxy-α-phenyl butyl nitrone and N-acetylcysteine. The entire disclosures of U.S. Provisional Application Ser. No. 60/833,114 filed on Jul. 25, 2006, and U.S. Provisional Application Ser. No. 60/833,452 filed on Jul. 26, 2006, are incorporated herein by reference. Additionally, the entire disclosures of pending U.S. application Ser. No. 12/374,970 and published PCT Application, Publication No. 2008/013866, are incorporated herein by reference.

SUMMARY OF THE INVENTION

In one embodiment, the current invention provides a method for treating hearing loss. In the method of the current invention, a pharmaceutically effective amount of a composition comprising 2,4-disulfonyl α-phenyl tertiary butyl nitrone is particularly useful for treating AAT-induced hearing loss.

In another embodiment, the current invention provides a method for treating hearing loss. In the method of the current invention, a pharmaceutically effective amount of a composition comprising 2,4-disulfonyl α-phenyl tertiary butyl nitrone and N-acetylcysteine is particularly useful for treating AAT-induced hearing loss.

Additionally, the present invention is directed to a method of treating AAT-induced hearing loss by orally administering a pharmaceutically effective amount of a composition comprising 2,4-disulfonyl α-phenyl tertiary butyl nitrone and N-acetylcysteine (NAC).

In yet another embodiment, the current invention provides a composition suitable for treating hearing loss resulting from oxidative stress such as may be induced by AAT. The composition comprises a pharmaceutically effective amount of 2,4-disulfonyl α-phenyl tertiary butyl nitrone. Preferably, the composition is suitable for oral administration to a patient.

Still further, the current invention provides a composition suitable for treating hearing loss resulting from oxidative stress such as may be induced by AAT. The composition comprises pharmaceutically effective amounts of 2,4-disulfonyl α-phenyl tertiary butyl nitrone and N-acetylcysteine. Preferably, the composition is suitable for oral administration to a patient.

In another embodiment, the current invention provides a composition comprising 2,4-disulfonyl α-phenyl tertiary butyl nitrone and N-acetylcysteine. The individual components of this composition may be at less than pharmaceutically effective amounts yet the combination thereof is pharmaceutically effective for treating sensorineural hearing loss.

DETAILED DESCRIPTION OF THE PREFERRED EMBODIMENTS OF THE CURRENT INVENTION

Figure 1:
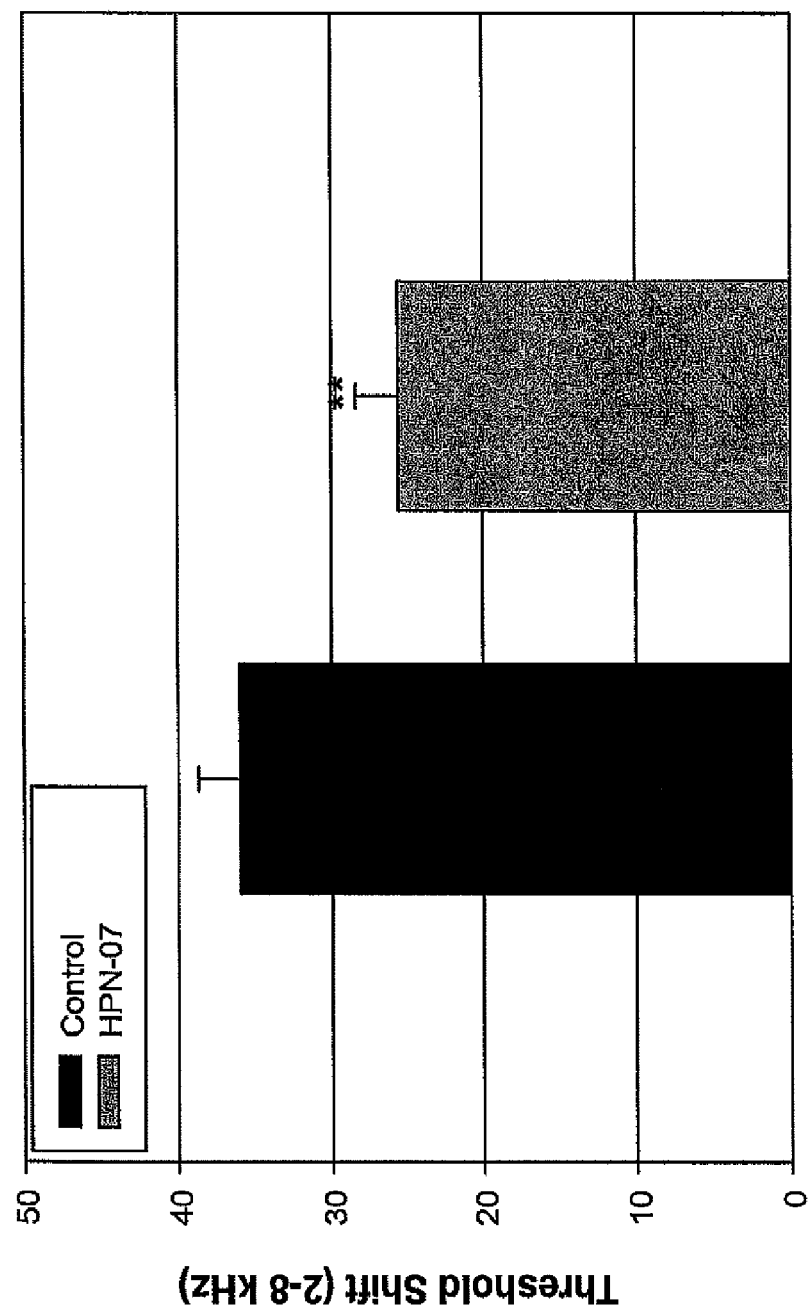
FIG. 1 corresponds to Example 1 and demonstrates the combined average threshold shift at all frequencies tested (2, 4, 6 and 8 kHz) in control and 2,4-disulfonyl PBN (HPN-07) treated subjects.

This invention provides methods for treating sensorineural hearing loss resulting from AAT and likely other causes of deafness related to oxidative stress, programmed cell death, or inflammatory processes. Examples of other causes of SNHL include but are not limited to, age related hearing loss or presbyacusis, toxin-induced hearing loss, trauma induced hearing loss, viral or bacterial infection leading to hearing loss, hearing loss due to prematurity, hearing loss due to cochlear ischemia, congenital hearing loss, genetic hearing loss, Meniere's disease, sudden hearing loss, and hearing loss related to thyroid disorders or diabetes mellitus. The current invention demonstrates the functionality of 2,4-disulfonyl α-phenyl tertiary butyl nitrone as a free radical trap and the synergistic effect of combining the 2,4-disulfonyl α-phenyl tertiary butyl nitrone with N-acetylcysteine (NAC) in the treatment of AAT. For the purposes of the remainder of this disclosure, 2,4-disulfonyl α-phenyl tertiary butyl nitrone will be referred to as 2,4-disulfonyl PBN or HPN-07.

The 2,4-disulfonyl PBN has the following structure:

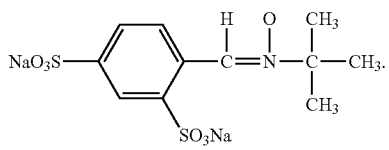

The acid form of the compound has the following structure:

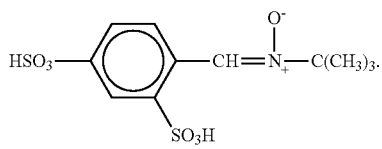

The acid form may be a solid or found in low pH solutions. The ionized salt form of the compound exists at higher pH and may be represented by either of the following structures:

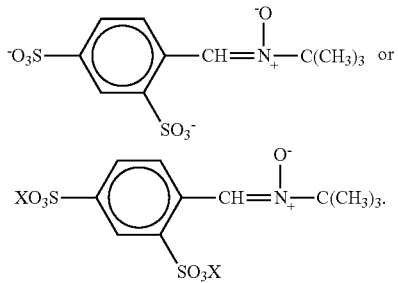

In the salt form, X is a pharmaceutically acceptable cation. Most commonly, this cation is a monovalent material such as sodium, potassium or ammonium, but it can also be a multivalent alone or cation in combination with a pharmaceutically acceptable monovalent anion, for example calcium with a chloride, bromide, iodide, hydroxyl, nitrate, sulfonate, acetate, tartrate, oxalate, succinate, palmoate or the like anion; magnesium with such anions; zinc with such anions or the like. Among these materials, the free acid and the simple sodium, potassium or ammonium salts are most preferred with the calcium and magnesium salts also being preferred but somewhat less so. The 2,4-disulfonyl PEN compound is described in detail by U.S. Pat. No. 5,488,145. The entire disclosure of U.S. Pat. No. 5,488,145 is incorporated herein by reference. The salts of 2,4-disulfonyl PBN may also be used for the treatment of AAT in a manner similar to the use of 2,4-disulfonyl PBN as discussed below.

Additionally, antioxidant peptides, which target the mitochondria, are useful in the present invention and may be included as part of the composition for treating AAT. These compounds preclude the generation of intracellular reactive oxygen species (ROS) which leads to oxidative stress and damage of the mitochondria. Oxidative damage of the mitochondria is known to cause apoptosis and necrosis leading to cell death. The preferred antioxidant peptides are Szeto-Schiller (SS) peptides and their functional analogs. These compounds have alternating aromatic residues and basic amino acids. In particular, peptides having tyrosine (Tyr) or dimethyltyrosine (Dmt) analogs can scavenge oxyradicals. These compounds inhibit oxidation of low-density lipoproteins. SS-peptides include compounds such as SS-31 (D-Arg-Dmt-Lys-Phe-$NH_2$) and SS-02 (Dmt-D-Arg-Phe-Lys-$NH_2$). In addition to the Tyr and Dint containing SS-peptides, tryptophan containing SS-peptides are also useful in the current invention. Finally, the amino acids found in the SS-peptides may be L or D and may be naturally occuring, non-naturally occuring and derivatives of naturally occuring amino acids. In particular, the SS-peptides disclosed in PCT published application WO 2005/072295 are suitable for use in the current invention. The entire disclosure of WO 2005/072295, published on Aug. 11, 2005 is incorporated herein by reference.

Thus, the current invention provides methods and compositions suitable for treating the referenced hearing conditions. In a preferred embodiment, the current invention utilizes 2,4-disulfonyl PBN and N-acetyleysteine to treat AAT. The composition of the current invention may optionally include additional antioxidant componds including, but not limited to, Acetyl-L-Carnitine (ALCAR), glutathione monoethylester, ebselen, D-methionine.

The compositions of the current invention will preferably be administered orally; however, other delivery methods including, but not limited to, intravenously, subcutaneously, by inhalation, sublingually, subdermally or locally within the ear are also suitable. Further the active composition may be administered as a nanoparticle or dendrimer formulation. The nanoparticle may be multifunctional and composed of a polymer and paramagnetic iron oxide particles to allow the application of external magnetic forces to aid in the delivery of the drug to the desired target such as the inner ear. Additionally, the composition may be formulated with additives known to those skilled in the art to enhance oral absorbtion and alter bioavailability kinetics.

Without wishing to be limited by theory, we believe that at least part of the functionality of 2,4-disulfonyl PBN results from its ability to inhibit the activity or up regulation of inducible nitric oxide synthase (iNOS). iNOS is responsible for activating neural inflammation which may increase the effect of oxidative stress or other injury to the inner ear tissues.

We have discovered that 2,4-disulfonyl PBN given as an oral administration to *chinchillas* that have been exposed to an AAT significantly protected them from hearing loss due to AAT. The data demonstrating this functionality is presented in FIGS. 1-2, 4A and 4B. Furthermore, we have discovered that antioxidants such as NAC are also effecting in protecting from AAT-induced hearing loss and provide a synergistic effect when used in combination with 2,4-disulfonyl PBN. The data demonstrating this functionality is presented in FIGS. 3, 4A-B and 5A-D.

For the experiments and examples described herein, the following methods were generally employed except for those described with respect to FIG. 5. Female adult *chinchilla laniger* (Mouton *Chinchilla* Ranch, Rochester, Minn.) weighing 500-850 grams were placed, two at a time, in two small wire restraint cages on a wooden plate where the AAT was induced by a 105 dB SPL octave-band noise centered at 4 kHz for 6 hours in a sound isolation booth [Industrial Acoustics Company (IAC), New York, N.Y.]. The noise was digitally generated by a Tucker Davis Technologies (TDT, Alachua, Fla.) device and passed through a real time attenuator (TDT, RP2), filtered, amplified with a preamplifier (QSC audio power, Costa Mesa, Calif.), and transduced with a high frequency acoustic driver and an acoustic speaker (JBL 2350, Northridge, Calif.) suspended from the ceiling of the sound booth which is placed directly above the wire cages. Before noise exposure, the sound spectrum output of the system was calibrated with a sound level meter centered at an octave bandwidth of 4 kHz. A condenser microphone (B&K 2804, Norcross, Ga.) coupled to the preamplifier was placed between the two wire cages at the level of the animals' heads to monitor the noise level. During noise exposure, the noise level was continually and visually monitored using the PULSE software system [B&K Sound & Vibration Measurement (version 10.0), Norcross, Ga.] including FFT Analysis Type 7770 and CPB Analysis 7771.

Figure 3:
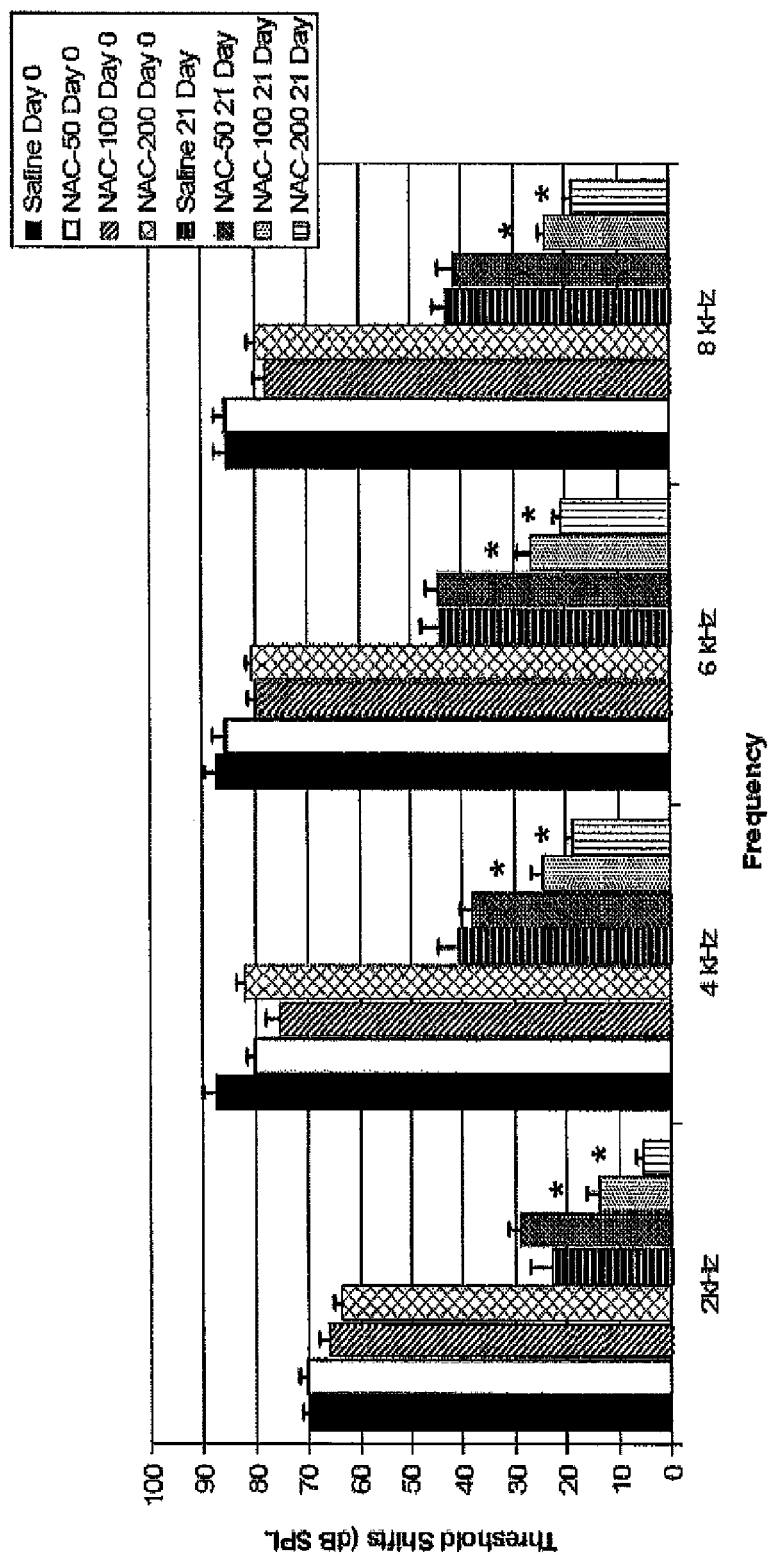
FIG. 3 corresponds to Example 2 and demonstrates the average threshold shift at 2, 4, 8 and 16 kHz in subjects treated with NAC at the indicated doses and time points post-AAT.
Figure 4A:
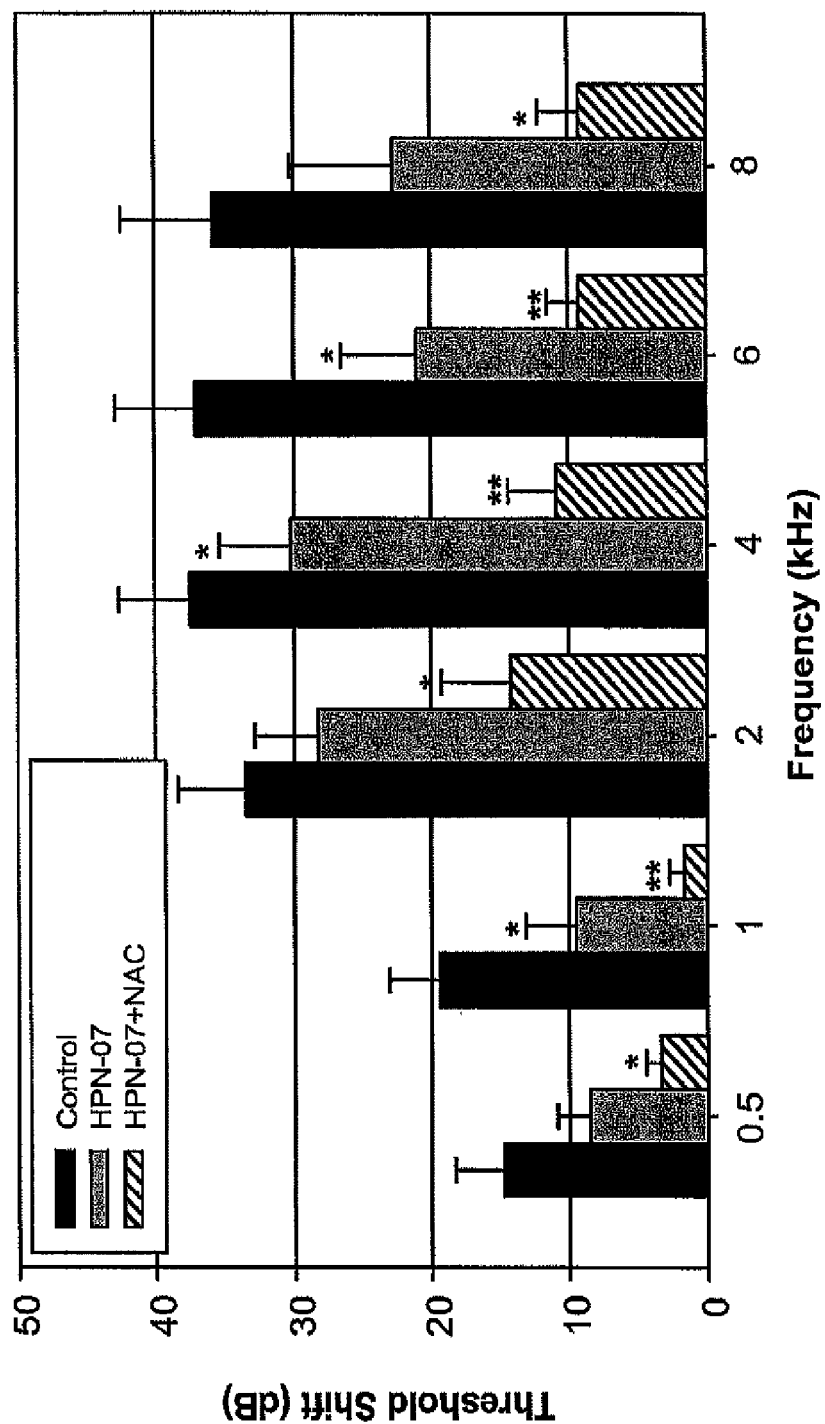
FIG. 4A corresponds to Example 3 and demonstrates the average threshold shift at each individual frequency (0.5, 1, 2, 4, 6 and 8 kHz) in control, 2,4-disulfonyl PBN (HPN-07) and 2,4-disulfonyl PBN (HPN-07)+NAC treated subjects.
Figure 4B:
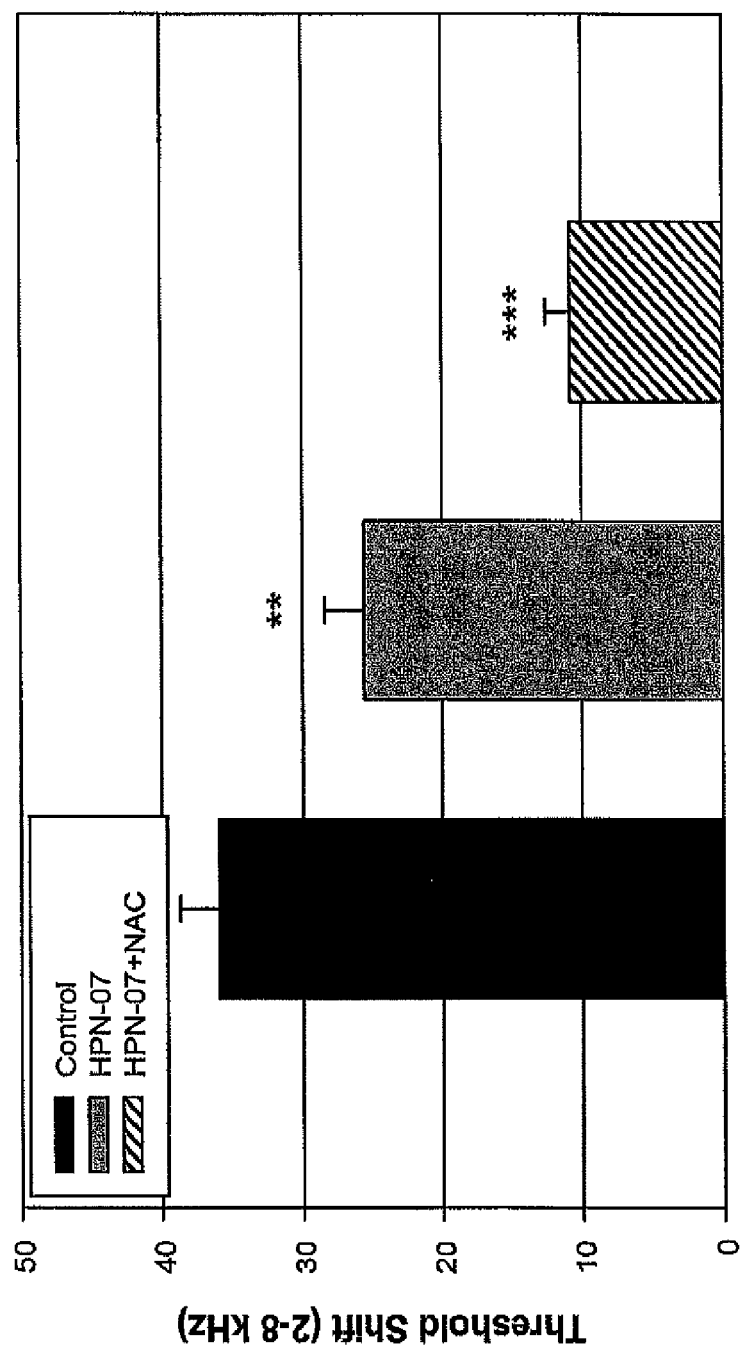
FIG. 4B corresponds to Example 3 and demonstrates the combined average threshold shift at all frequencies tested (2, 4, 6 and 8 kHz) in control, 2,4-disulfonyl PBN (HPN-07) and 2,4-disulfonyl PBN (HPN-07)+NAC treated subjects.
Figure 5A:
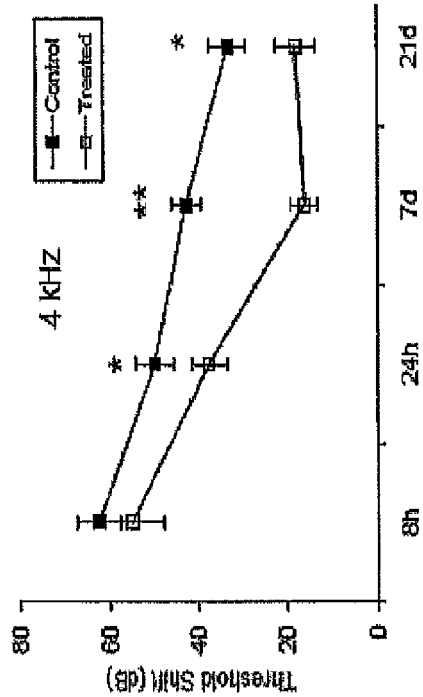
FIG. 5A corresponds to Example 3 and demonstrates the average threshold shift at 2 kHz in subjects treated with 2,4-disulfonyl PBN (HPN-07)+NAC at the indicated time points post AAT.
Figure 5B:
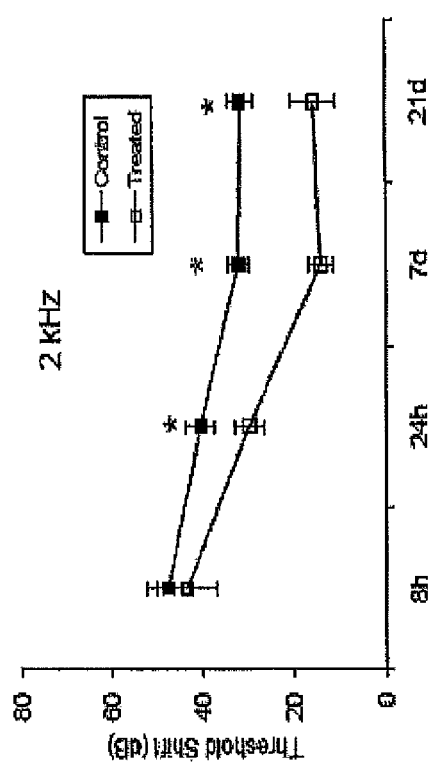
FIG. 5B corresponds to Example 3 and demonstrates the average threshold shift at 4 kHz in subjects treated with 2,4-disulfonyl PBN (HPN-07)+NAC at the indicated time points post AAT.
Figure 5C:
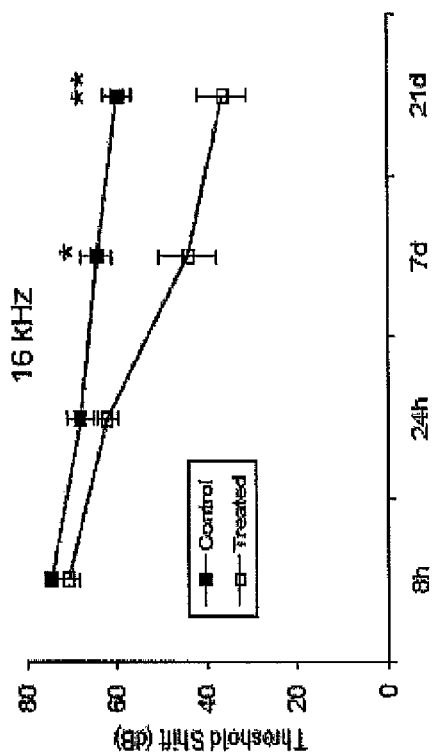
FIG. 5C corresponds to Example 3 and demonstrates the average threshold shift at 8 kHz in subjects treated with 2,4-disulfonyl PBN (HPN-07)+NAC at the indicated time points post AAT.
Figure 5D:
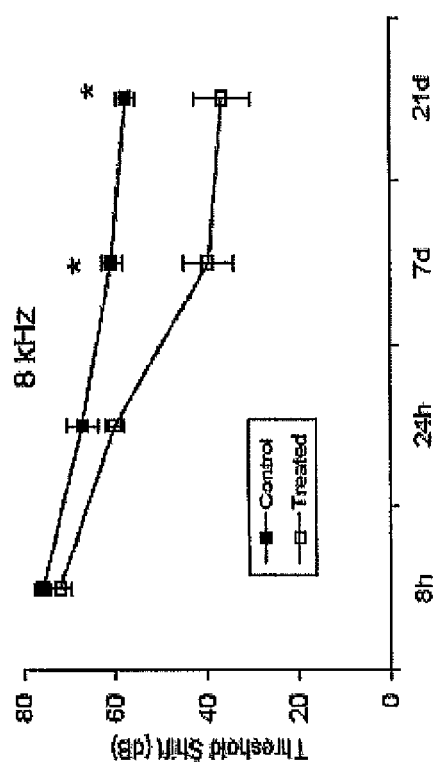
FIG. 5D corresponds to Example 3 and demonstrates the average threshold shift at 16 kHz in subjects treated with 2,4-disulfonyl PBN (HPN-07)+NAC at the indicated time points post AAT.

Subjects were administered one of the following treatments ("mg/kg" denotes mg of compound per kg body weight):
(1) 300 mg/kg 2,4-disulfonyl PBN (HPN-07; FIGS. 1-2, 4A-B);
(2) 50 mg/kg of NAC (NAC-50; FIG. 3);
(3) 100 mg/kg of NAC (NAC-100; FIG. 3);
(4) 200 mg/kg of NAC (NAC-200; FIG. 3);
(4) 300 mg/kg 2,4-disulfonyl PBN+300 mg/kg of NAC (HPN-07+NAC; FIGS. 4A-B and 5); or
(5) control—10% sucrose solution (oral) or saline (intraperitoneal) (FIGS. 1-5).

The treatments were administered a total of five times including one dose 4 hours post-AAT, and two doses daily on days 1 and 2 post AAT.

Hearing was assessed as auditory brainstem response (ABR) which was measured at between 1 and 3 days prior to AAT and at one or more of the following time points post AAT: 1 hr, 8 hr, 24 hr 7 day and 21 days. The 21 day test point was considered the permanent threshold shift (PTS). ABR recordings were performed under light ketamine (20 mg/kg) and xylazine (1 mg/kg) anesthesia. Small supplemental doses (⅓ of initial dose) were given if needed. ABR thresholds were recorded from subcutaneous needle electrodes placed under the skin of the head. An active needle electrode and a reference electrode were placed proximal to the right ear and the left ear, respectively while a ground electrode was placed at the vertex. Auditory stimuli was generated using a computer-aided system (Intelligent Hearing Systems, Miami, Fla.) coupled to high frequency transducers. Acoustic stimuli were tone pips (5 ms duration and 1 ms Blackman rise and fall) at frequencies of 0.5, 1, 2, 4, 6, 8, and 16 kHz. All acoustic stimuli were transduced through the computer-controlled attenuator to a 3A insert earphone [Etyniotic Research (ER)-3A, Etymotic Research Inc., Elk Grove Village, Ill.] placed about 5 mm from the tympanic membrane. The insert earphone was calibrated with a coupler mounted to the sound level meter approximating its placement. The electrical responses obtained from the electrodes were amplified (×100,000), filtered (100-3,000 Hz), and digitized through an A/D converter on a signal processing board. They were averaged at a sample rate of 1024 for each level.

Hearing thresholds were tested in 10 dB descending steps until near the threshold, and then 5 dB ascending steps were taken to determine the threshold. Threshold was defined as the midpoint between the lowest level of a clear response and the next level where no response was observed. The threshold shift refers to the difference in threshold prior to and following AAT. The investigators performing the ABR measurements were blinded as to the identity of the animal groups.

Example 1

The purpose of this example is to demonstrate that 2,4-disulfonyl PBN (HPN-07) is effective to treat hearing loss induced by AAT.

Figure 2:
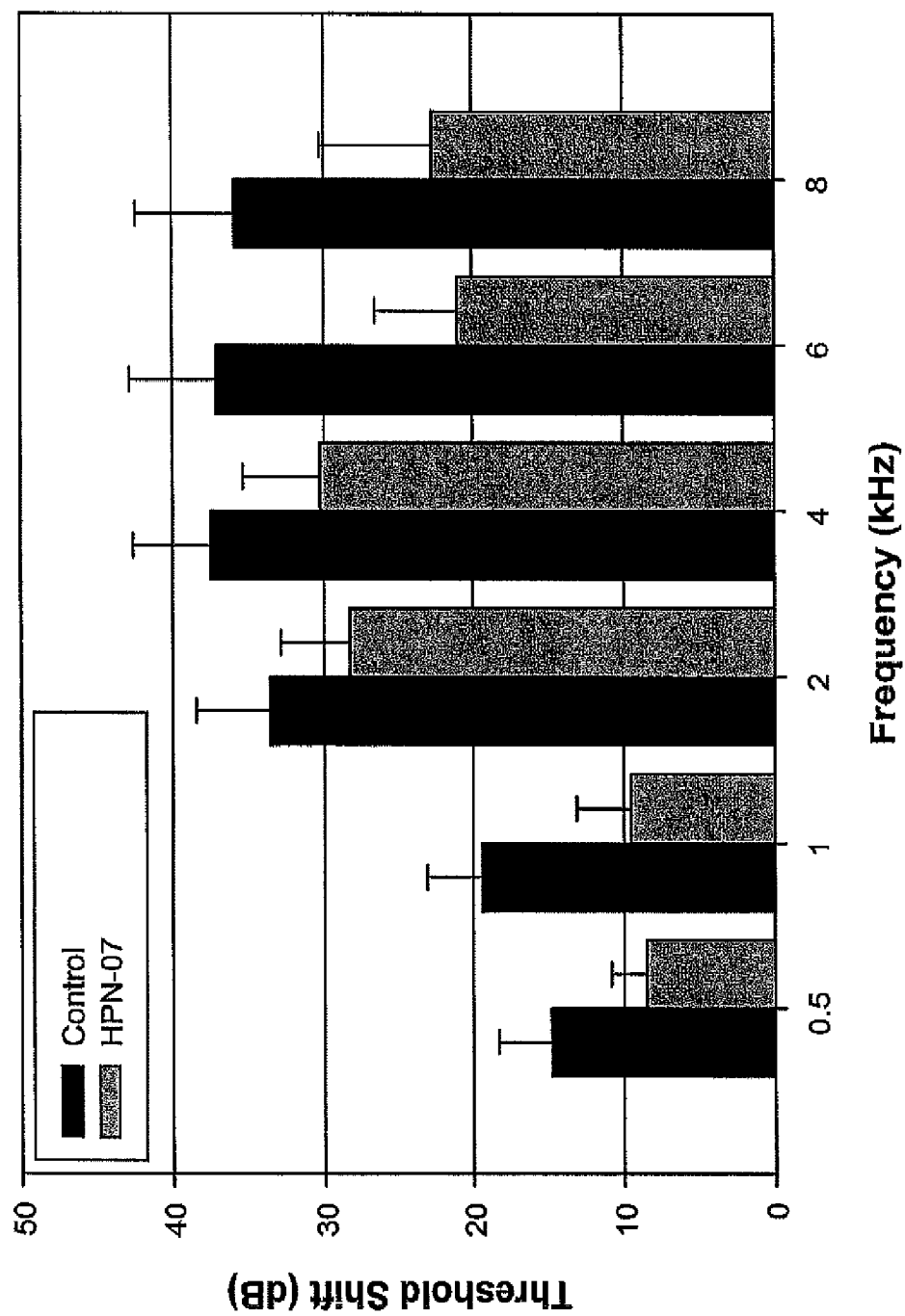
FIG. 2 corresponds to Example 1 and demonstrates the average threshold shift at each individual frequency (0.5, 1, 2, 4, 6 and 8 kHz) in control and 2,4-disulfonyl PBN (HPN-07) treated subjects.

All data values in FIGS. 1 and 2 are represented as means±SEM. Statistically significant differences in threshold shifts were tested via ANOVA (SPSS 14.0 for Windows). Frequency was treated as within subject factor while treatment was the between-subjects factor. When a main effect was found, post-hoc tests such as LSD and Tukey was performed for mean comparisons among different groups. A p-value less than 0.05 represents a statistically significant difference.

FIG. 1 represents the average threshold shift across all frequencies tested at 21 days post AAT. As demonstrated therein, adult *chinchillas* receiving HPN-07 (n=5) had a significantly decreased average threshold shift compared to control animals not receiving the compound (n=6). As demonstrated in FIG. 2, the most pronounced effect of HPN-07 occurred at 0.5, 1, 6 and 8 kHz, while the effect was less prominent at 2 and 4 kHz. This suggests that animals receiving HPN-07 were able to detect the test tone at a lower decibel value than control animals. Effective results should be realized at dosages between 5 mg/kg and about 300 mg/kg for 2,4-disulfonyl PBN. Additionally, in view of the resulting ABR data, one would expect a statistically significant reduction in outer hair cell loss in animals heated with 2,4-disulfonyl PBN when compared to the control group of animals. In sum, FIGS. 1 and 2 demonstrate that 2,4-disulfonyl PBN improves hearing in animals exposed to AAT.

Example 2

The purpose of this example is to demonstrate the effectiveness of NAC in treating hearing loss in an animal model.

Six *chinchillas* per experimental group were administered either saline (control), 50,100, or 200 mg/kg of NAC via intraperitoneal (i.p.) injection at 4 hours post AAT exposure. Statistical analysis was performed using a two way ANOVA and Post hoc test, "*" denotes a p<0.05.

As depicted in FIG. 3, NAC demonstrates a mild effect on threshold shift soon after treatment. However, at 21 days following AAT exposure, there is a significant decrease in threshold shift in animals receiving 100 mg/kg and 200 mg/kg of NAC. These results demonstrate that antioxidants, such as NAC, are effective in treating hearing loss associated with AAT.

Example 3

The purpose of this example is to demonstrate the effectiveness of 2,4-disulfonyl PBN in combination with NAC for treating hearing loss in an animal model.

FIGS. 4A and 4B illustrate the synergistic effect of a combination treatment comprising NAC and 2,4-disulfonyl PBN. In this example, *chinchillas* were orally administered either control (10% sucrose) (n=6), HPN-07 (n=5) or HPN-07+NAC (n=3). Threshold was measured 21 days post AAT. Data in FIG. 4A represents the average threshold shift for each individual frequency tested. The data in FIG. 4B represents the combined average threshold shift data from 2 kHz to 8 kHz. Data were analyzed via a two-way ANOVA, Bonferroni test "" denotes a p value of less than 0.01 and "*" denotes a p value of less than 0.001.

Threshold shifts were found in the control group and treated groups at all frequencies with greater shifts in the high frequencies (2-8 kHz). See FIG. 4A. As demonstrated in FIG. 4A, treatment with HPN-07 alone resulted in a significant reduction in threshold shift at 0.5, 1, 4 and 6 kHz. The addition of NAC to the HPN-07 treatment composition resulted in a significant reduction in threshold shift across all frequencies tested. Furthermore, the combined data in FIG. 4B demonstrates an overall significant reduction in threshold shift when subjects were administered either HPN-07 alone or in combination with NAC. Moreover, FIGS. 4A and 4B clearly demonstrates that administration of NAC in combination with HPN-07 provides a more robust decrease in threshold shift as compared to treatment with HPN-07 alone. Taken together, these results support the use of 2,4-disulfonyl PBN and NAC in a combination therapy for treating hearing loss.

FIG. 5A-D depicts the effects of HPN-07+NAC on hearing loss (threshold shift) as a function of time in a rat model of AAT. Rats were randomly assigned to either treatment or control groups which consisted of 6 rats per time point (8 h, 24 h, 7 d and 21 d) post AAT. In order to induce AAT, rats were anesthetized with ketamine/xylazine and exposed for 1 h to 115 dB SPL one-octave band noise centered at 14 kHz. HPN-07 (300 mg/kg) in combination with NAC (300 mg/kg) was administered via i.p. injection one hour after noise exposure and then administered twice a day on days 1 and 2 post AAT. Controls received the same volume of saline at the same time points. The Figure shows average ABR threshold shifts with error bars at each time point. Data were analyzed via a two-way ANOVA, Bonferroni test, *p<0.05, **p<0.01.

First, it should be noted that the hearing loss produced in the rat model was substantially greater than that observed in the *chinchilla* model (50-70 dB threshold shift compared to approximately 35 dB, respectively). As demonstrated in FIGS. 5A and 5B, the HPN-07+NAC combination treatment was successful in significantly reducing the threshold shift as early as 24 hours post AAT (23 hours following administration of treatment). Furthermore, HPN-07+NAC treatment resulted in significant reduction in threshold shift at all frequencies at 7 and 21 days post AAT. In light of the severity of the hearing loss demonstrated in the rat model, the results in FIGS. 5A-D demonstrate that the combination of 2,4-disulfonyl PBN with NAC is extremely effective in reducing permanent hearing loss.

In general it is expected that treatment of hearing loss resulting from AAT should begin as soon as possible. For treatment of other types of sensorineural hearing loss treatment using the methods and compositions described herein will vary depending on the cause of hearing loss. For example hearing loss due to age may require delivery of one of the above described compositions on a regular treatment schedule such daily, alternating days or weekly depending on the nature of the hearing loss. In cases relating to hearing loss resulting from toxins or radiation, treatment should begin as soon as possible and will likely conclude upon restoration of hearing.

The current disclosure demonstrates the effectiveness of 2,4-disulfonyl PBN in treating subjects subjected to AAT. In particular, the use of 2,4-disulfonyl PBN as a treatment for AAT has been shown to at least reduce hearing loss in subjects that have experienced AAT. In addition, the combination of 2,4-disulfonyl PBN with NAC produces a synergistic result and further reduces hearing loss.

As used herein, a "pharmaceutically effective amount" is an amount of a pharmaceutical compound or composition having a therapeutically relevant effect on hearing loss. A therapeutically relevant effect relates to some improvement in hearing capacity or a change in the cellular, physiological or biochemical parameters associated with any of the causes of sensorineural hearing loss including but not limited to age related hearing loss or presbyacusis, toxin-induced hearing loss, trauma induced hearing loss, viral or bacterial infection leading to hearing loss, hearing loss due to prematurity, hearing loss due to cochlear ischemia, congenital hearing loss, genetic hearing loss, Meniere's disease, sudden hearing loss, and hearing loss related to thyroid disorders or diabetes mellitus. 2,4-disulfonyl PBN and NAC may be administered in dosages which are pharmaceutically effective for each compound, or in dosages which are sub-clinical, i.e., less than pharmaceutically effective for each, or a combination thereof, provided that the combined dosages are pharmaceutically effective.

Typically, a composition comprising 2,4-disulfonyl PBN with NAC will have two parts NAC for every part of 2,4-disulfonyl PBN, i.e. a ratio of 2:1, NAC to 2,4-disulfonyl PBN. Thus, the concentration of NAC used in the composition of NAC with 2,4-disulfonyl PBN will be substantially less than treatment of a patient with NAC alone. Based on the examples provided herein, the compositions may comprise between about 70 mg and about 1200 mg of 2,4-disulfonyl PBN and from about 700 mg and about 4000 mg of NAC. Furthermore, compositions comprising 2,4-disulfonyl PBN may be administered at a dose of between about 1 mg/kg to about 400 mg/kg body weight and more likely around 300 mg/kg body weight. Compositions comprising NAC may be administered at a dose of between about 5 mg/kg to about 300 mg/kg body weight. These ranges are based on the examples included herein and do not limit the range of pharmaceutically effective amounts for other organisms.

One skilled in the art from a reading of this disclosure will likely recognize related compounds which will also provide satisfactory results. Further, although the foregoing examples treated the test subjects four hours post AAT, treatments administered within shorter time periods should be as effective and will likely be preferred. In addition, treatments administered longer than 48 hour post AAT, stress or injury may also be effective. As such the foregoing disclosure is merely considered to be exemplary of the current invention with the true scope of the current invention being defined by the claims.

We claim:

1. A method for treating sensorineural hearing loss, comprising orally delivering to a patient in need thereof a composition comprising a pharmaceutically effective amount of 2,4-disulfonyl α-phenyl tertiary butyl nitrone.

2. The method of claim 1, wherein said composition further comprises N-acetylcysteine.

3. The method of claim 2, wherein first delivery of said composition occurs within four hours following an event causing the sensorineural hearing loss.

4. The method of claim 2, wherein said composition is delivered at least two times within twenty-four hours following an event causing the sensorineural hearing loss.

5. The method of claim 3, wherein the event causing the sensorineural hearing loss is an acute acoustic trauma event.

6. The method of claim 4, wherein the event causing the sensorineural hearing loss is an acute acoustic trauma event.

7. The method of claim 1, wherein said composition is delivered within four hours following an event causing the sensorineural hearing loss.

8. The method of claim 1, wherein said composition is delivered at least two times within twenty-four hours following an event causing the sensorineural hearing loss.

9. The method of claim 7, wherein the event causing the sensorineural hearing loss is an acute acoustic trauma event.

10. The method of claim 8, wherein the event causing the sensorineural hearing loss is an acute acoustic trauma event.

* * * * *

UNITED STATES PATENT AND TRADEMARK OFFICE
CERTIFICATE OF CORRECTION

| | |
|---|---|
| PATENT NO. | : 10,555,915 B2 |
| APPLICATION NO. | : 13/391772 |
| DATED | : February 11, 2020 |
| INVENTOR(S) | : Kopke et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 662 days.

Signed and Sealed this
Sixth Day of December, 2022

Katherine Kelly Vidal
*Director of the United States Patent and Trademark Office*